(12) United States Patent
Doskocil

(10) Patent No.: US 11,400,277 B2
(45) Date of Patent: Aug. 2, 2022

(54) NEUROMODULATION ELECTRODE ASSEMBLY

(71) Applicant: TESLA MEDICAL S.R.O., Ostrava (CZ)

(72) Inventor: Lukas Doskocil, Ostrava (CZ)

(73) Assignee: Tesla Medical S.R.O, Ostrava-Pustkovec (CZ)

( * ) Notice: Subject to any disclaimer, the term of this patent is extended or adjusted under 35 U.S.C. 154(b) by 184 days.

(21) Appl. No.: 16/755,651

(22) PCT Filed: Oct. 11, 2018

(86) PCT No.: PCT/EP2018/077798
§ 371 (c)(1),
(2) Date: Apr. 13, 2020

(87) PCT Pub. No.: WO2019/073003
PCT Pub. Date: Apr. 18, 2019

(65) Prior Publication Data
US 2020/0282201 A1    Sep. 10, 2020

(51) Int. Cl.
*A61N 1/04* (2006.01)
*A61N 1/32* (2006.01)
(Continued)

(52) U.S. Cl.
CPC .......... *A61N 1/0452* (2013.01); *A61M 21/00* (2013.01); *A61N 1/321* (2013.01); *A61M 21/02* (2013.01);
(Continued)

(58) Field of Classification Search
CPC .......... A61M 21/00–02; A61N 1/0452; A61N 1/0456; A61N 1/0484; A61N 1/0492;
(Continued)

(56) References Cited

U.S. PATENT DOCUMENTS 3,967,628 A * 7/1976 Vredenbregt ............ A61B 5/25
  607/149
8,938,303 B1 * 1/2015 Matsen ............... A61N 1/36021
  607/48
(Continued)

FOREIGN PATENT DOCUMENTS

CZ    2015467 A3    1/2017
CZ    2015468 A3    1/2017
(Continued)

OTHER PUBLICATIONS

International Search Report & Written Opinion related to Application No. POT/EP2018/077798 dated Oct. 11, 2017.
(Continued)

*Primary Examiner* — Thaddeus B Cox
(74) *Attorney, Agent, or Firm* — von Briesen & Roper, s.c.

(57) ABSTRACT

An effective neuromodulation electrode assembly configured to provide a precise neuromodulation of a desired nerves whilst forming an efficient electro conductive interface between a patient skin and the neuromodulation electrode. The neuromodulation electrode comprising an enclosure having on one side a protrusion extending up to an end having an opening, an electrical interface, an electro conductive electrode piece coupled to the electrical interface on one end and having the opposite end configured to interact with a patient skin. The electrode piece further comprising, an electrically conductive solid element coupled on one side to the electrical interface and an electrically conductive soft
(Continued)

deformable element that projects outwards through the opening and which adapted to form an interface between the solid element and the patient skin.

13 Claims, 6 Drawing Sheets

(51) Int. Cl.
*A61M 21/02* (2006.01)
*A61M 21/00* (2006.01)
*A61N 1/36* (2006.01)

(52) U.S. Cl.
CPC .. *A61M 2021/0055* (2013.01); *A61N 1/36025* (2013.01)

(58) Field of Classification Search
CPC ............ A61N 1/04–0496; A61N 1/321; A61N 1/36014–36046; A61N 1/36021; A61N 1/36025
See application file for complete search history.

(56) References Cited

U.S. PATENT DOCUMENTS

| | | |
|---|---|---|
| 2003/0004555 A1 | 1/2003 | Giuntoli et al. |
| 2006/0094948 A1* | 5/2006 | Gough ................. A61B 5/6831 600/372 |
| 2009/0157149 A1 | 6/2009 | Wahlgren et al. |
| 2011/0093035 A1 | 4/2011 | Moser et al. |
| 2014/0228927 A1 | 8/2014 | Ahmad et al. |
| 2016/0213936 A1* | 7/2016 | Heerlein .............. H04R 25/554 |

FOREIGN PATENT DOCUMENTS

| | | |
|---|---|---|
| JP | S50119485 A | 9/1975 |
| JP | 2011505981 A | 3/2011 |
| JP | 2013508015 A | 3/2013 |
| WO | WO 2017132067 A2 | 8/2017 |

OTHER PUBLICATIONS

Japanese Search Report related to Application No. 2020-520454; dated Apr. 21, 2021.

* cited by examiner

US 11,400,277 B2

NEUROMODULATION ELECTRODE ASSEMBLY

CROSS-REFERENCE TO RELATED APPLICATION

This Application is a 35 USC § 371 US National Stage filing of International Application No. PCT/EP2018/077798 filed on Oct. 11, 2018 and claims priority under Czech Application No. PV 2017-647 filed on Oct. 11, 2017.

FIELD OF THE DISCLOSURE

Embodiments of the present disclosure generally relate to a neuromodulation of a tibial and a peroneal nerve, transcutaneous modulation of sacral spinal roots or other nerves suitable for the neuromodulation. More particularly, the embodiments relate to a neuromodulation electrode enabling an effective transfer of a neuromodulation signal from a signal generator onto the target nerve.

BACKGROUND OF THE DISCLOSURE

This section provides background information related to the present disclosure which is not necessarily prior art.

Electrical neuromodulation has been used for a treatment of pain, urinary incontinence, mental and other difficulties, as well as for the prevention of vascular disease, as disclosed for instance in U.S. Pat. No. 5,358,513.

Traditional systems utilize neuromodulation electrodes in the form of a body invasive needle electrodes inserted into the immediate vicinity of the nerve to be stimulated. Insertion of the needle electrodes into the immediate vicinity of the nerve is always associated with a risk of a nerve damage and/or an introduction of an infection into the body of a patient.

In recent years a new non-invasive method using electrodes made of metal was described for instance in CZ 2015-468 and CZ 2015-467. Such electrodes were used for instance with success for a nerve neuromodulation in an incontinence treatment. The non-invasive method describes bipolar electrodes for multiple uses, having electrodes made of metal, for example made of stainless steel coated with silver, enabling a modulation of a desired nerve. Such electrodes would be placed with their respective ends onto a stimulation point on a patient's skin. The described electrodes bear a disadvantage that their respective ends often do not provide a good contact with the skin over the desired surface area due to manufacturing defects of the electrodes caused for example by an uneven surface machining, surface impurities and other defects or due to physiological effects such as skin wrinkling, pores, or hairs. This causes differences of the electrode to skin contact area and may result in a skin/tissue damage, which is unacceptable. The smaller the contact area of the electrode is with the skin, the greater the issue becomes. Additionally the desired contact area of the electrode with the skin varies upon many conditions. For instance obese patients have typically a higher resistance skin that consequently requires a higher intensity of the stimulating current flowing through the electrodes to the skin, which can result in exceeding the safe threshold of about 2 mA/cm2. Thin patients have typically the skin resistance lower and therefore the stimulating current intensity does not need to be as high.

The electrodes known from the above-mentioned state of the art do not allow to achieve an effective surface area contact of the electrodes with the skin. Moreover, due to the hygiene requirements, these electrodes need to be disinfected after each use, which introduces additional microscratches on the electrode surface and further worsen the contact. The cost of the electrodes is relatively high and their frequent replacement would be a cost prohibitive.

Therefore, it would be advantageous to have an apparatus that takes into account at least some of the issues discussed above as well as possibly other issues.

SUMMARY OF THE DISCLOSURE

According to various aspects of the present disclosure, exemplary embodiments of a neuromodulation electrode assembly comprising an enclosure having on one side a protrusion extending up to an end having an opening, an electrical interface adapted to be coupled to an external apparatus, an electro conductive electrode piece coupled to the electrical interface on one end and having the opposite end configured to interact with a patient skin via a portion of the electrode piece that projects outwards through the opening. The electrode piece further comprising, an electrically conductive solid element coupled on one side to the electrical interface and an electrically conductive soft deformable element that projects outwards through the opening and which adapted to form an interface between the solid element and the patient skin.

In embodiments of the neuromodulation electrode assembly, one may use one and/or several of the following features and any combination thereof:

- the protrusion has a shape chosen from: a substantially conical shape, a substantially pyramidal shape, a bell shape, a substantially frustoconical shape, a substantially cylindrical shape, a substantially cuboid shape, a substantially prismatic shape or a substantially polygonal shape;
- the electrically conductive soft deformable element is made of a material chosen from a gel, a rubber, a polymer or a paraffin with or without an electrically conductive filament;
- the conductive soft deformable element is at least partially hollow and said electrically conductive solid element is received within said conductive soft deformable element;
- the electrically conductive soft deformable element has a contact portion which covers said electrically conductive solid element and has a thickness comprised between 0.005 and 15 mm;
- the electrically conductive soft deformable element has an electrical resistance between 0Ω to 250Ω;
- the enclosure further comprises a base from which extends said protrusion, said protrusion being removably attached to the base, said electrically conductive solid element being rigid with the base and the electrically conductive soft deformable element being held between said protrusion and said base;
- the removable holder is attached to the base by snap fitting and/or at least one screw or an adhesive layer or a hook and loop fastener;
- the protrusion is hollow and covers a support portion belonging to the base, said support portion having a shape substantially complementary to the protrusion and protruding from the base up to a apex formed by the electrically conductive solid element, the electrically conductive soft deformable element being held between said support portion and said protrusion;
- the enclosure further comprises a base from which extends said protrusion, said base being coupled to an attachment member adapted to secure a position of the neuromodulation electrode against the skin of a patient;

the attachment member is configured to be able to encircle a patient limb;

the attachment member is one of a strap, a belt, a chain or a clip;

the attachment member comprises a positioning element for an angular positioning of the neuromodulation electrode against the skin of the patient;

the positioning element comprises of a cushion;

the cushion is moveable along the attachment member.

Further areas of applicability will become apparent from the description herein. The description and specific examples in the summary are intended for purposes of illustration only and are not intended to limit the scope of the present disclosure.

BRIEF DESCRIPTION OF THE DRAWINGS

Other features and advantages of the invention appear from the following detailed description of some of its embodiments, given by way of non-limiting example, and with reference to the accompanying drawings, in which.

MORE DETAILED DESCRIPTION

As used herein, an element or step recited in the singular and proceeded with the word "a" or "an" should be understood as not excluding plural of the elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In the figures, the same references denote identical or similar elements, unless stated otherwise.

Figure 1:
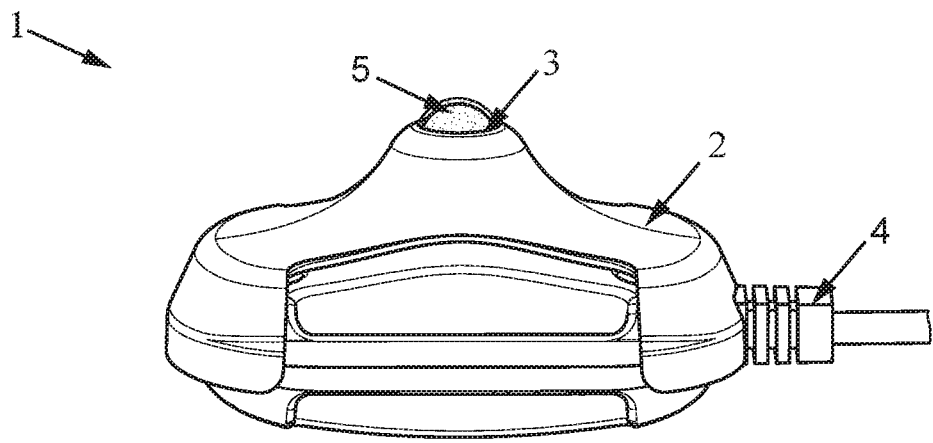
FIG. 1 is a perspective view of an exemplary embodiment of the neuromodulation electrode assembly, in a configuration of use.

FIG. 1 illustrates a perspective view of an exemplary embodiment of the neuromodulation electrode assembly 1. The embodiment comprises an enclosure having on one side a protrusion 2 extending up to an end having an opening 3. An electrical interface 4 is adapted to be coupled to an external apparatus that may provide a signal for the neuromodulation. The neuromodulation electrode assembly 1 may further comprises an electro conductive piece 5 that may be coupled to the electrical interface 4 on one end and having the opposite end configured to interact with a patient skin via a portion of the electrode piece 5 that projects outwards through the opening. The electrode piece may comprises an electrically conductive solid element 15, 16 coupled on one side to the electrical interface. The electrode piece may further comprises an electrically conductive soft deformable element that projects outwards through the opening 3 and which may be adapted to form an interface between the solid element and the patient skin. Advantageously, the size of opening 3 may be variable.

The protrusion 2 may have a shape chosen from: a substantially conical shape, a substantially pyramidal shape, a bell shape, a substantially frustoconical or frustopyramidal, shape, a substantially cylindrical shape, a substantially cuboid shape, a substantially prismatic shape or a substantially polygonal shape. The electrically conductive soft deformable element may be made of a material chosen from a gel, a rubber, a polymer or a paraffin with or without an electrically conductive filament. The electrically conductive filament 7, 14 may be made of a carbon, a carbide, a graphene, an electrically conductive liquid or electrically conductive solid material such as for instance metal.

Preferably, the electrically conductive soft deformable element may be made of a hydrogel being a hydrophilic-material-based gel that may be suspended in a water. The hydrophilic-material-based gel may be composed of one or more polymers, potassium carbonate and a cellulose or silicone-based material.

Preferably, the electrically conductive soft deformable element may be removable and may be configured to be easily replaceable. Preferably, the electrically conductive soft deformable element may be made by a foil or a flexible film it may be further capable to adapt to the shape of the protrusion 2 and a support portion 12.

Preferably, the electrically conductive soft deformable element may be made of a hydrogel. The hydrogel may be made via one of an inkjet/extrusion printing, a wet-spinning and/or a physical cross-linking. The electrically conductive soft deformable element may be a part or a coating.

Preferably the electrically conductive soft deformable element thickness ranges from 0.05 mm to 55 mm, even more preferably 0.05 mm to 15 mm and even more preferably 0.05 mm to 10 mm.

Preferably, the conductive soft deformable element has a contact portion which covers the electrically conductive solid element and has a thickness between 0.005 and 15 mm.

Preferably, the electrically conductive soft deformable element has an electrical resistance between $0\Omega$ to $250\ k\Omega$.

The neuromodulation electrode assembly may be electrically coupled via the electrical interface 4 to an external apparatus, which may provide an electrical signal with a desired waveform. The waveform frequency may be preferably set between 1 Hz to 20 Hz or even more preferably, set to the frequency between 2 Hz to 6 Hz. The pulses may be monophasic or biphasic and, for example, right-angled, sinusoidal or triangular with exponential starts or ends and with widths from 0.1 ms to 5 ms, with amplitude from 0 mA up to 50 mA.

Figure 2:
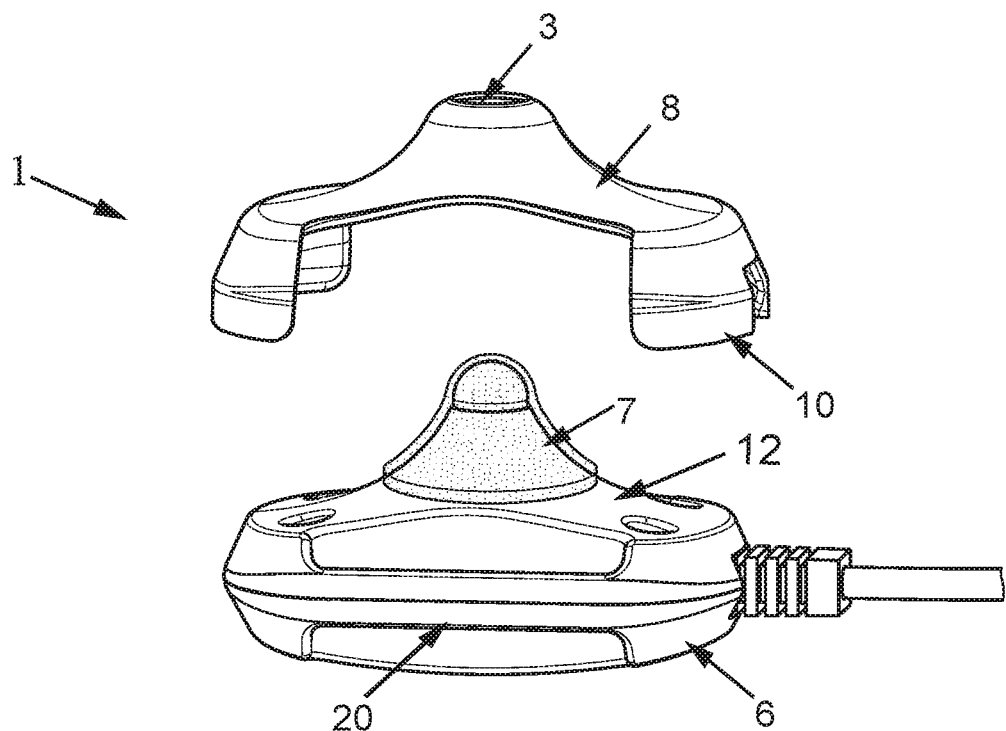
FIG. 2 is a view similar to FIG. 1 with a removable holder in a removed position.

FIG. 2 illustrates a perspective view of one embodiment that may be utilized with the exemplary neuromodulation electrode assembly. The enclosure may comprises a base 6 from which may extend the protrusion 2 that may be removably attached to the base 6. The electrically conductive solid element may be rigid with the base and the electrically conductive soft deformable element 7, 14 may be held between the protrusion 2 and the base 6. The conductive soft deformable element 7, 14 may be at least partially hollow and the electrically conductive solid element 16, 15 may be received within the conductive soft deformable element. Alternatively the electrically conductive solid element may be at least partially hollow and a portion of the conductive soft deformable element 7 may be received within the electrically conductive solid element.

The protrusion 2 may be hollow and may cover a support portion 12 belonging to the base 6. The support portion 12 may have a shape substantially complementary to the protrusion 2 and protruding from the base up to an apex formed by the electrically conductive solid element, the electrically conductive soft deformable element 7 may be held between the support portion 12 and the protrusion 2. Then the protrusion 2 that may be removably attached to the base 6 may form a removable holder 8 that may be attached to the base 6 by a snap fitting 10 and/or at least one screw or an adhesive layer or a Velcro®-type fastening (hook and loop fastener).

When the electrically conductive soft deformable element 7 is held in between the removable protrusion 2 that may form the removable holder 8 and the support portion 12 or the base 6 then the electrically conductive soft deformable element 7 may deform and may consequently form a flexible film capable to adapt to the shape of the electrically conductive solid element 16, 15 and may form an effective electrical interface with the skin and may provide an improved distribution of the neuromodulation signal. Through a variable size opening 3 that may be made in the removable protrusion 2 that may form removable holder 8 it may be possible to control how far the electrically conductive soft deformable element projects outwards through the opening 3. Advantageously, this may enable to adapt the interface between the electrically conductive soft deformable element and the patient skin. Advantageously, it may be possible to select a protrusion 2 that may form a removable holder 8 and features a corresponding diameter of opening 3 that depends on the physiological parameters of a given patient.

Therefore preferably, the protrusion 2 that may form a removable holder 8 may be made with the opening 3 having various diameters and/or shapes, consequently enabling a change in the surface area of the electrically conductive soft deformable element 7 that may form an interface between the neuromodulation electrode and the patient's skin, thereby, influencing the neuromodulation current distribution of the neuromodulation electrode to skin electrical interface.

Alternatively, the electrically conductive soft deformable element may be attached to the base 6 via a feature or a profile made in the base that would secure the electrically conductive soft deformable element in a position relative to the base. In another alternative embodiment the electrically conductive soft deformable element may be removeably attached to the base via an adhesive layer. In another alternative embodiment, the electrically conductive soft deformable element gel electrode may be held within the base as a result of the neuromodulation electrode being put in contact with the skin.

Figure 3:
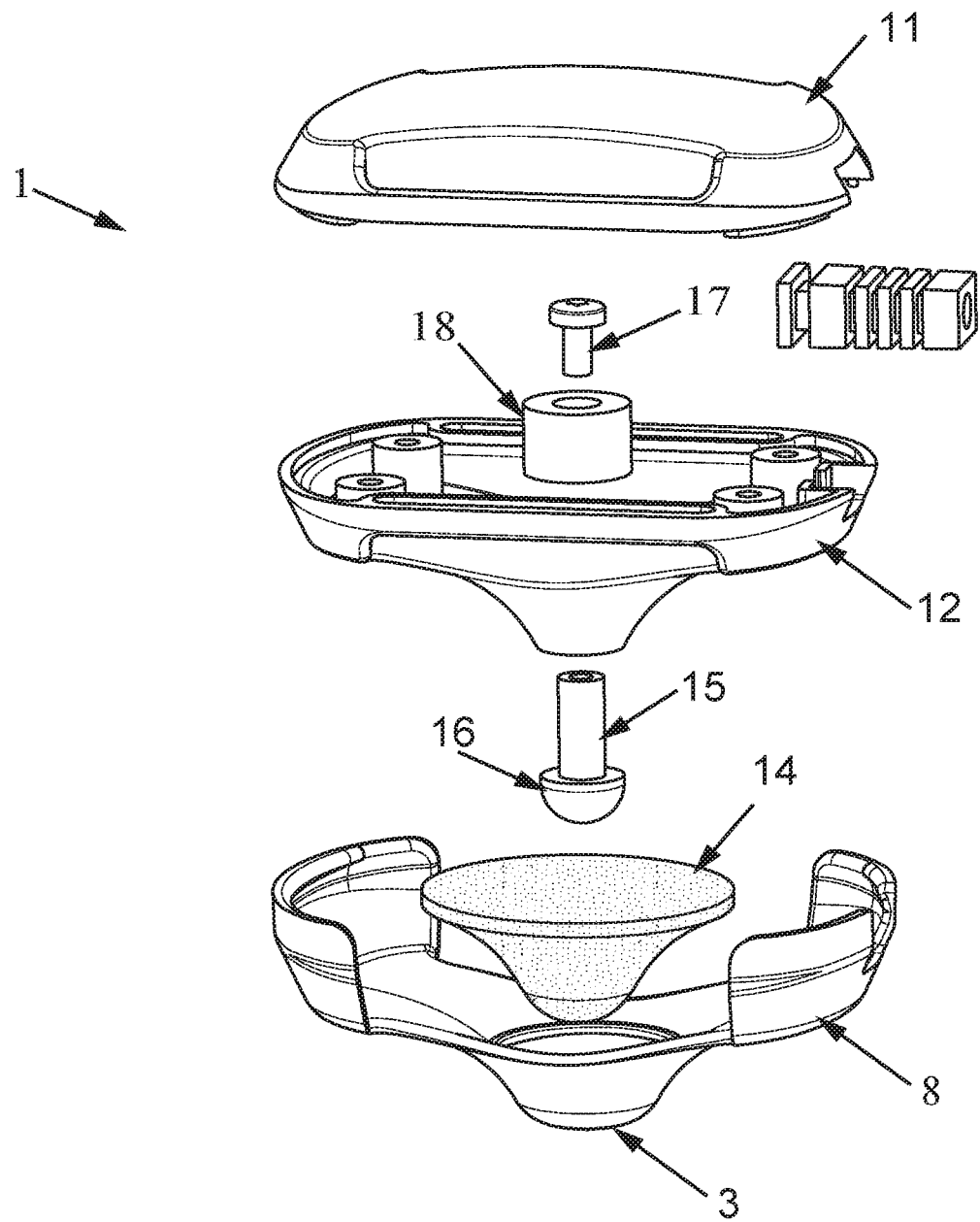
FIG. 3 is an exploded view of the neuromodulation electrode assembly of FIGS. 1 and 2.

FIG. 3 illustrates an exploded view that shows one possible embodiment of a configuration of the neuromodulation electrode assembly 1. The one possible embodiment of the neuromodulation electrode assembly 1 comprises the enclosure that may comprise the protrusion 2 that may form a removable holder 8 and may be coupled to the support portion 12 belonging to the base 6. The embodiment may further comprise a magnetic field source 18, an electrically conductive solid element 15 that may preferably have a shaped end 16 having a surface, an electrically conductive soft deformable element 14 and a means 17 to attach the magnetic field source 18 to the support portion 12 or the base 6. The shaped end 16 of the electrically conductive solid element 15 may be one of a semi-circular shape, a conical shape, a pyramidal shape, a bell shape, a substantially frustoconical or frustopyramidal shape, a substantially cylindrical shape, a substantially cuboid shape, a substantially prismatic shape or a substantially polygonal shape. The shape end 16 may be coated.

The magnetic field source 18 may be formed by at least one magnet. The magnetic field source 18 may be located inside or outside the enclosure. The magnetic field source 18 may be used to increase a depth range of neuromodulation signals transmitted by the neuromodulation electrode assembly 1. The magnetic field source 18 may be a permanent magnet or an electromagnet. The magnetic field source 18 may have a shape of a hollow cylinder configured to receive a portion of the electrically conductive solid element 15 within. In an alternative embodiment, the magnetic source 18 may be a group of magnets that may surround a portion of the electrically conductive solid element 15. The electrically conductive solid element 15 may be made of various materials, preferably of at least one of diamagnetic materials. The shaped end 16 of the element 15 may be formed from at least one of diamagnetic material such as precious metals, a brass, a copper, a carbon, a carbide for example. In an alternative embodiment, the electrically conductive solid element 15 may be in the form of an electro conductive plate that may have an inner side coupled to the electrical interface 4. Alternatively an electro conductive spring may be coupled to one side of the electrically conductive solid element 15, while the other end of the spring may be connected to the electrical interface 4 forming the electrical connection between the electrically conductive solid element 15 and the electrical interface 4. The electro conductive spring may be a coil spring, a compression type spring, a disc spring, a conical spring or a leaf spring. In such case the electrically conductive solid element 15 may be positively forced by the spring towards the electrically conductive soft deformable element 14 and that may be consequently forced to project outwards through the opening 3 and may form an outside surface of the shaped end 16 of the electrically conductive solid element 15.

Preferably, in case of an implementation of the magnetic field source 18 as a group of electromagnets, the magnetic field may be advantageously adjusted using a variable or a tunable excitation of at least one of the electromagnets. In such case the variable or tunable excitation may affect the direction of electrical energy flow from the neuromodulation electrode into a patient tissue. This may be advantageously utilized to find a desired nerve, even if the neuromodulation electrode is placed on the skin of a patient inaccurately.

Figure 4:
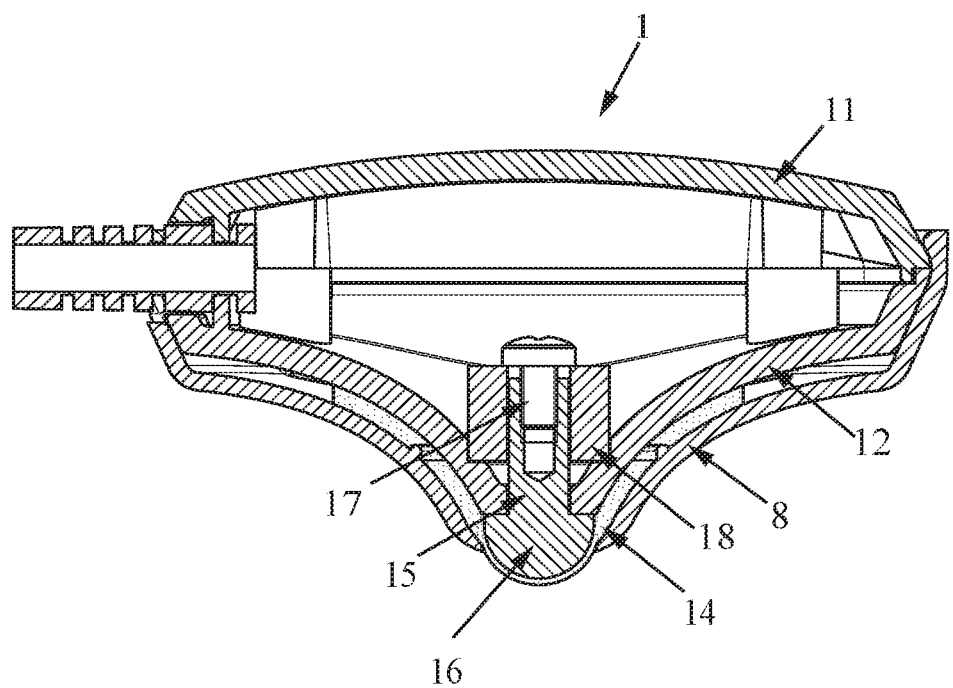
FIG. 4 is a side cross-sectional view of the neuromodulation electrode assembly of FIGS. 1-3.

FIG. 4 illustrates a side cross-sectional view of an exemplary embodiment depicted in the neuromodulation electrode assembly. In the embodiment the thickness of the electrically conductive soft deformable element 8, 14 placed between the protrusion 2 that may be formed by a removable holder 8 and the support portion 12 may be controlled via the shape of the protrusion 2 and mating surface of the support portion 12. Additionally or alternatively the thickness of the electrically conductive soft deformable element 14 may be controlled via the shaped end 16 of the electrically conductive solid element 15 and/or via the positive force that may be caused by the spring coupled to the electrically conductive solid element 15. The spring may be configured to force the electrically conductive solid element 15 outwards through the opening 3.

Figure 5:
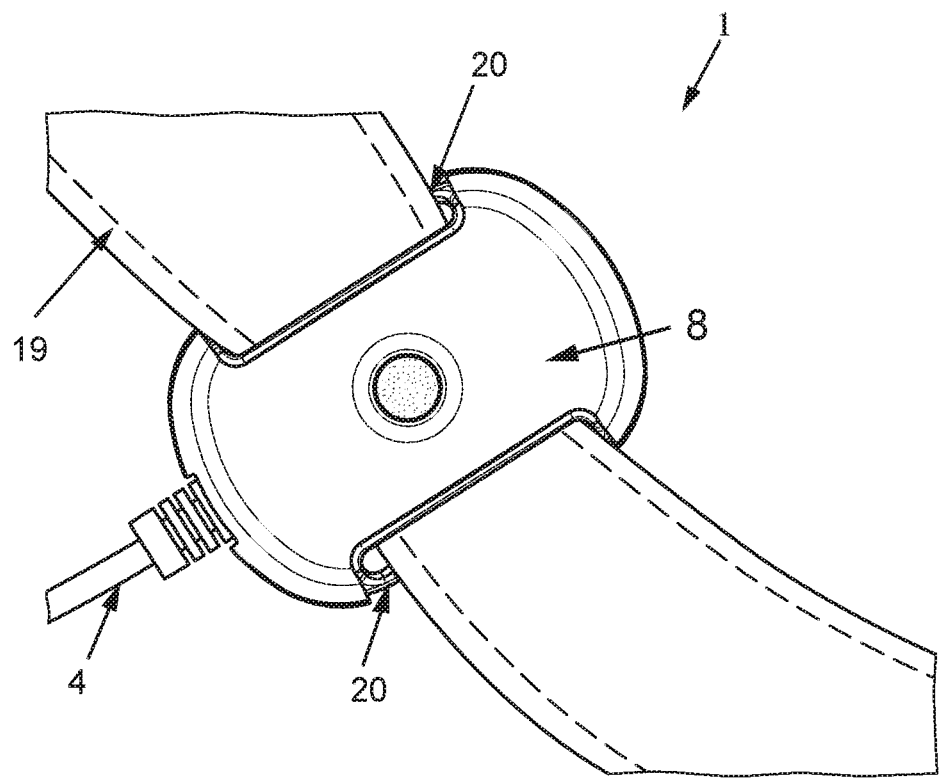
FIGS. 5 and 6 are respectively a bottom perspective view and a side perspective view of the neuromodulation electrode assembly of FIGS. 1-4, featuring an attachment member.

FIG. 5 illustrates a bottom perspective view of another embodiment featuring an attachment member that may be utilized with the exemplary neuromodulation electrode assembly. In the embodiment the enclosure further comprises an attachment member 19 coupled to the base 6. The attachment member may be adapted to secure a position of the electrode assembly against the skin in a particular positon. The attachment member 19 may be configured to be able to encircle a patient limb 23. Preferably the attachment member 19 may be made of one of a strap, a belt, a chain or a clip. Preferably the attachment member 19 may be coupled to the assembly through at least one opening 20 in at least one side of the base 6.

Figure 6:
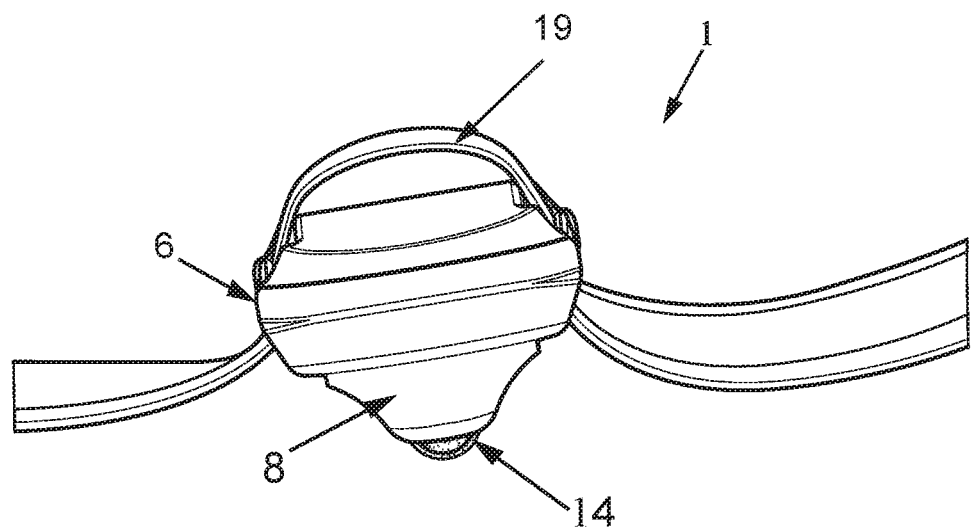

FIG. 6 illustrates a side perspective view of FIG. 5 featuring an attachment member 19 that may be utilized with the exemplary neuromodulation electrode assembly. It shows one possibility, where the attachment member 19 may be secured to the base of the enclosure. Preferably, the attachment member 19 may be made of a rubber, a neoprene, an elastomer, a leather, a plastic or other suitable material. Advantageously, the attachment member may be configured to control the depth of the neuromodulation electrode immersion into the limb 23 by controlling the electrode's preload against the limb 23 the attachment member is causing. This may be achieved by tensioning of the attachment member, in other words controlling how tight the attachment member encircles the patient limb 23. The electrically conductive soft deformable element may also be configured to contribute, due to its elasticity, to control the depth of the neuromodulation electrode immersion into the limb 23.

Figure 7:
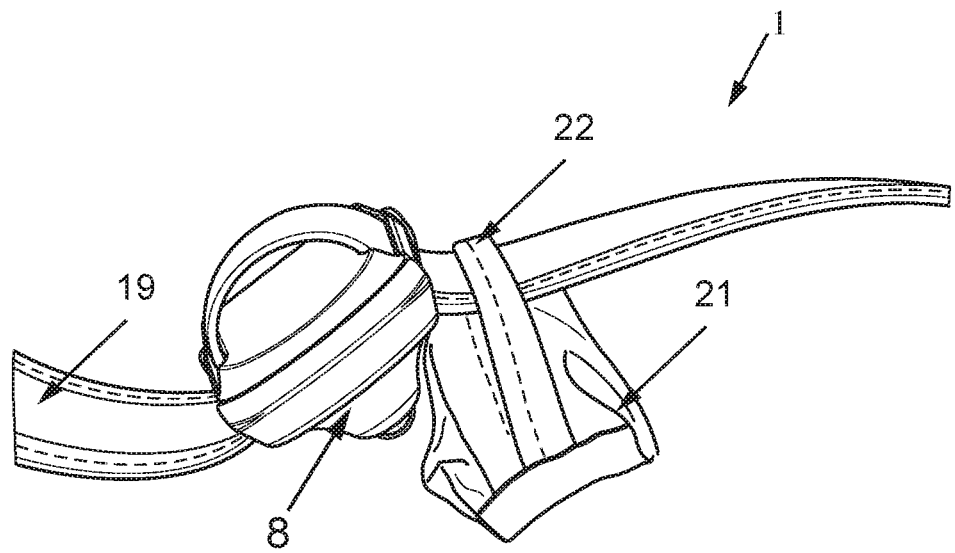
FIGS. 7 and 8 are perspective views of the assembly of FIGS. 5-6, additionally featuring a positioning element.
Figure 8:
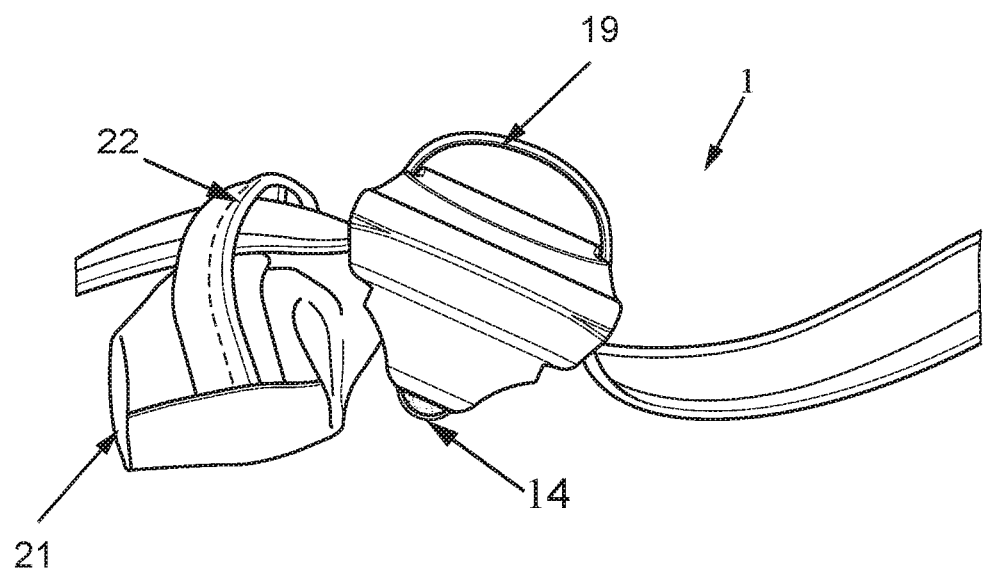

FIG. 7 and FIG. 8 illustrate a perspective view of another embodiment featuring a positioning element 21 that may be utilized with the exemplary neuromodulation electrode assembly. In the embodiment the attachment member comprises a positioning element that may be used for an angular positioning of the neuromodulation electrode against the skin of a patient. Preferably the positioning element 21 may be coupled to the attachment member 19 via one of a strap, a belt, a chain or a clip. Preferably the positioning element comprises at least one of a cushion, a pad, a pillow or a solid or semi-solid piece. Preferably, the positioning element 21 may be moveably attached to attachment member (21). Preferably, the positioning element may be moveable along the attachment so that it may be moved along and/or around the limb.

Figure 9:
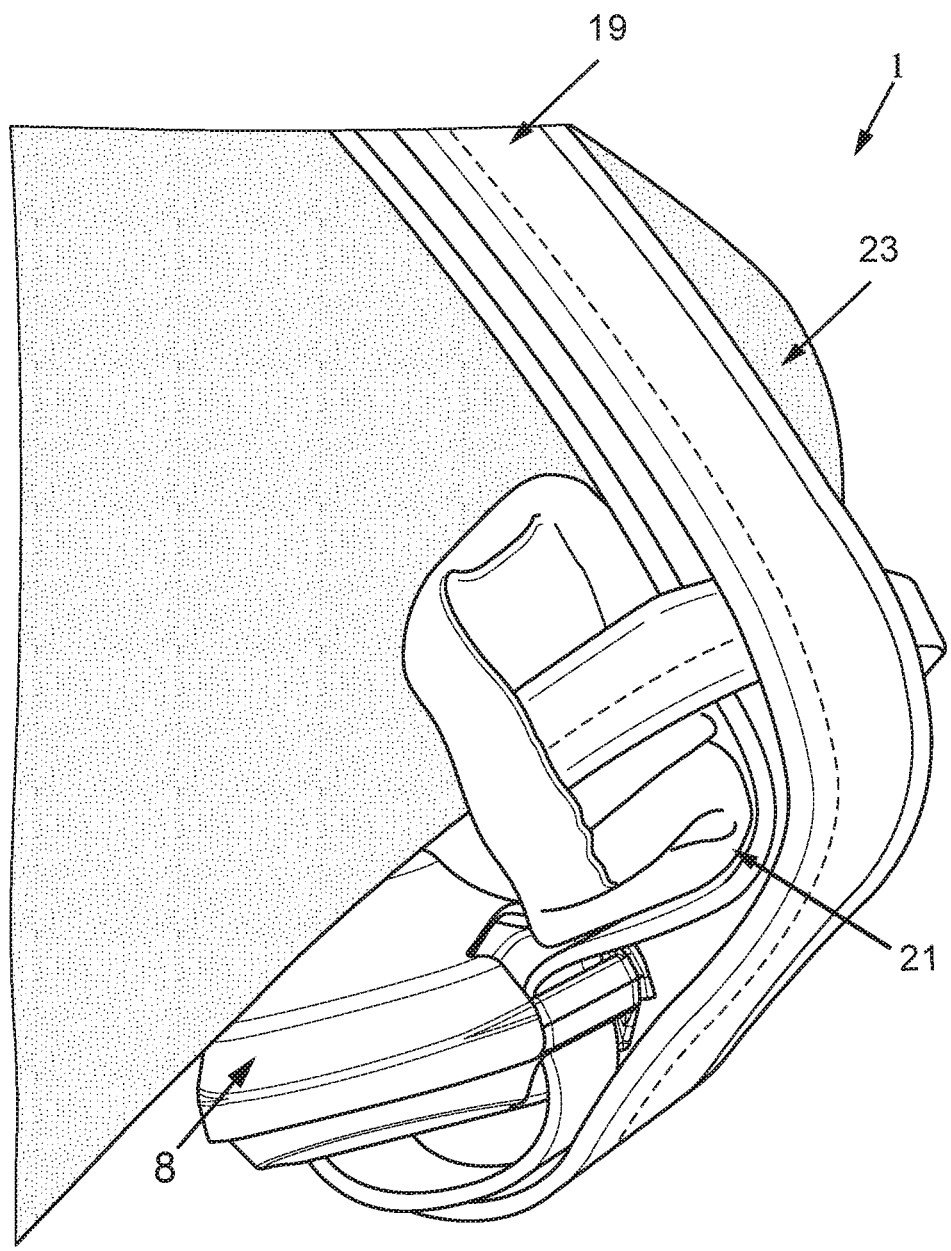
FIG. 9 is a perspective view of the assembly of FIGS. 7-8 being attached to a limb.

FIG. 9 illustrates a perspective view of another embodiment of the exemplary neuromodulation electrode assembly being attached to a limb 23. The embodiment shows an advantageous positioning of neuromodulation electrode where the positioning element 21 may be configured to enable a movement and/or an angular tilt of the neuromodulation electrode to reach and/or secure the most advantageous position of the neuromodulation electrode for the neuromodulation of a particular nerve. This enables to reach a correct location placement of the neuromodulation electrode that is crucial for the effectiveness of the neuromodulation procedure and eliminates a risk of the procedure efficiency reduction due to improper location placement of the neuromodulation electrode.

Further, the disclosure comprises embodiments according to the following clauses:

Clause 1. A stimulation electrode of an apparatus for neuromodulation comprising an enclosure and an electrical conductive element terminated by an electrically conductive surface, wherein the electrode further comprising a removable gel electrode electrically coupled with a generator of an electrical signal through the electrically conductive surface.

Clause 2. The stimulation electrode of Clause 1, wherein the stimulation electrode further comprising a source of magnetic field inside or outside of the enclosure.

Clause 3. The stimulation electrode of Clause 2, wherein the electrical conductive element protrudes through a magnetic field created by at least one magnet.

Clause 4. The stimulation electrode of Clause 2 or 3, wherein the magnet is one of a permanent magnet or an electromagnet.

Clause 5. The stimulation electrode of Clause 1, wherein a holder of the gel electrode is removeably attached to the enclosure.

Clause 6. The stimulation electrode of Clause 5, wherein the holder comprises elastically deformable elements that at least partially encircle the enclosure or the holder is equipped with an element equipped with a thread mountable to the enclosure.

Clause 7. The stimulation electrode of Clause 5 or 6, wherein the enclosure has an opening for the gel electrode placement, wherein the opening holds the gel electrode in place.

Clause 8. The stimulation electrode of Clause 1, wherein the gel electrode is part of the support portion having an opening into which is the gel electrode inserted.

Clause 7. The stimulation electrode of Clause 1, wherein the thickness of the gel electrode is between 0.005 mm to 5 mm.

Clause 10. The stimulation electrode of Clause 1, wherein the gel electrode is made of an electro conductive material having an electrical resistance between 0Ω až 250Ω.

The above-mentioned embodiments may offer an effective neuromodulation electrode assembly configured to provide a precise neuromodulation of a desired nerves whilst forming an efficient electro conductive interface between a patient skin and the neuromodulation electrode. Additionally the electrically conductive soft deformable element may represents a low cost disposable accessory.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims.

The invention claimed is:

1. An assembly of a neuromodulation electrode comprising:
    an enclosure having on one side a protrusion extending up to an end having an opening;
    an electrical interface adapted to be coupled to an external apparatus;
    an electro conductive electrode piece coupled to the electrical interface on one end and having an opposite end configured to interact with a patient skin via a portion of the electrode piece that projects outwards through the opening, the electrode piece comprising:
    an electrically conductive solid element coupled on one side to the electrical interface; and
    an electrically conductive soft deformable element that projects outwards through the opening and which is adapted to form an interface between the solid element and the patient skin,
    wherein the enclosure further comprises a base from which extends the protrusion, the protrusion being removably attached to the base, the electrically conductive solid element being rigid with the base, wherein the removable protrusion is hollow and covers a support portion belonging to the base, the support portion having a she complementary to the protrusion and protruding from the base up to an apex formed by the electrically conductive solid element, the electrically conductive soft deformable element being held between the support portion and the protrusion.

2. The assembly according to claim 1, wherein the protrusion has a shape chosen from: a conical shape, a pyramidal shape, a bell shape, a frustoconical shape, a cylindrical shape, a cuboid shape, a prismatic shape or a polygonal shape.

3. The assembly according to claim 1, wherein the electrically conductive soft deformable element is made of a material chosen from a gel, a rubber, a polymer or a paraffin with or without an electrically conductive filament.

4. The assembly according to claim 1, wherein the conductive soft deformable element is at least partially hollow and the electrically conductive solid element is received within the conductive soft deformable element.

5. The assembly according to claim 1, wherein the electrically conductive soft deformable element has a contact portion which covers the electrically conductive solid element and has a thickness comprised between 0.005 and 15 mm.

6. The assembly according to claim 1, wherein the electrically conductive soft deformable element has an electrical resistance between 0Ω to 250Ω.

7. The assembly according to claim 1, wherein the removable protrusion is attached to the base by snap fitting and/or at least one screw or an adhesive layer or a hook and loop fastener.

8. The assembly according to claim 1, wherein the base being coupled to an attachment member and is adapted to secure a position of the neuromodulation electrode against the skin of a patient.

9. The assembly according to claim 8, wherein the attachment member is configured to be able to encircle a patient limb.

10. The assembly according to claim 8, wherein the attachment member is one of a strap, a belt, a chain or a clip.

11. The assembly according to claim 8, wherein the attachment member comprises a positioning element for an angular positioning of the neuromodulation electrode against the skin of the patient.

12. The assembly according to claim 11, wherein the positioning element comprises of a cushion.

13. The assembly according to claim 12, wherein the cushion is moveable along the attachment member.

* * * * *

UNITED STATES PATENT AND TRADEMARK OFFICE
CERTIFICATE OF CORRECTION

PATENT NO. : 11,400,277 B2
APPLICATION NO. : 16/755651
DATED : August 2, 2022
INVENTOR(S) : Lukas Doskocil It is certified that error appears in the above-identified patent and that said Letters Patent is hereby corrected as shown below:

On the Title Page

Item (71), delete the words "TESLA MEDICAL S.R.O., Ostrava, (CZ)" and substitute therefore --STIMVIA S.R.O., Ostrava-Pustkovec, (CZ)--.

Signed and Sealed this
Twenty-fifth Day of July, 2023

Katherine Kelly Vidal
*Director of the United States Patent and Trademark Office*